United States Patent [19]

Goldberg et al.

[11] Patent Number: 4,664,660
[45] Date of Patent: May 12, 1987

[54] CHEST DRAINAGE APPARATUS WITH AMBIENT AIR SEALING

[75] Inventors: Edward M. Goldberg, Glencoe; Seymour Bazell, Skokie, both of Ill.

[73] Assignee: Becton, Dickinson and Company, Franklin Lakes, N.J.

[21] Appl. No.: 718,519

[22] Filed: Apr. 1, 1985

[51] Int. Cl.$^4$ .............................................. A61M 1/00
[52] U.S. Cl. ..................................... 604/321; 206/363
[58] Field of Search ................................. 604/317–323, 604/326, 327, 335, 115, 126, 164, 165, 167, 324; 206/363, 438, 370; 128/DIG. 26, 760, 763, 764, 765, 766, 770, 774

[56] References Cited

U.S. PATENT DOCUMENTS

| | | | |
|---|---|---|---|
| 2,815,025 | 12/1957 | Fenton et al. | 604/335 |
| 3,463,159 | 8/1969 | Heimlich | 128/350 |
| 3,547,119 | 12/1970 | Hall et al. | 604/164 |
| 4,134,512 | 1/1979 | Nugent | 128/764 |
| 4,332,322 | 1/1982 | Jaeschke et al. | 206/363 |
| 4,435,171 | 3/1984 | Goldberg et al. | 604/343 |

FOREIGN PATENT DOCUMENTS

0111087  6/1984  European Pat. Off. ............ 604/319

Primary Examiner—C. Fred Rosenbaum
Assistant Examiner—J. L. Kruter
Attorney, Agent, or Firm—Welsh & Katz, Ltd.

[57] ABSTRACT

Apparatus for drainage of a body cavity includes a housing body defining an inlet chamber and a discharge chamber, with the former having a catheter mounted to one wall thereof and communicating with the inlet chamber, and a one-way elongated valve of the type disclosed in U.S. Pat. No. 3,463,159, and commonly known as the Heimlich valve, in fluid communication between the inlet chamber and the drainage chamber. An inlet port is provided in another wall of the housing body defining the inlet chamber which is adapted to reversibly receive a trocar and enable at least a portion of the trocar to pass through the inlet chamber and the catheter to enable the insertion of the catheter into the body cavity to be drained. In one embodiment, a collar is provided to support the open, inlet end of the sleeve of the one-way valve and a bellows-shaped member is provided to support the collar, valve and discharge chamber in spaced relation to the body housing portion defining the inlet chamber. In another embodiment, the inlet end of the sleeve of the one-way valve is fitted to a port of the inlet chamber housing and, optionally, a band thereover can be heat shrunk thereto. A hydrophobic filter is provided along one wall of the discharge chamber to filter gaseous fluids therefrom. Discharge and suction means can also be provided to the discharge chamber.

33 Claims, 13 Drawing Figures

CHEST DRAINAGE APPARATUS WITH AMBIENT AIR SEALING

This invention relates generally to catheter apparatus, and more particularly to an improved intrapleural catheter apparatus and combined apparatus for installing the improved intrapleural catheter.

BACKGROUND OF THE INVENTION

Catheter apparatus, particularly useful for the drainage of the chest cavity, i.e. the region surrounding the lungs, in the treatment of certain chest injuries, illnesses and in post-operative treatment, was disclosed in U.S. Pat. No. 3,463,159. The apparatus disclosed in the patent, commonly known as the Heimlich valve, has been a successful improvement over earlier catheters in providing means for continuous drainage of the chest cavity, while eliminating the need for cumbersome drainage apparatus, particularly apparatus requiring water traps, such as those shown in U.S. Pat. Nos. 3,363,626; 3,363,627; 3,559,647 and 3,683,913.

While the Heimlich valve is quite useful, it must be used with additional apparatus to insert a catheter into the boy cavity to be drained, to connect the catheter to the valve and to provide for discharge of fluids removed from the body cavity from the discharge of the valve. It has been necessary to obtain the additional apparatus, usually from several sources, and to assure the sterility of each of the components to be placed in communication with the body cavity or in the area of the patient's body in which the catheter is to be inserted. Moreover, while the use of the Heimlich valve permitted rapid emergency treatment and transportation of patients, the additional apparatus frequently restricted the freedom of movement of the patient.

It is therefore an object of the present invention to provide compact, self-contained means for the drainage of a body cavity.

It is another object of the present invention to provide body cavity drainage apparatus in which a catheter is preassembled to the drainage valve apparatus, and the entire assembly is lightweight and portable.

Still another object of the invention is to provide a self-contained sterile kit which can be readily used for drainage of a body cavity.

These and other objects, features and advantages of the present invention will become apparent from the following description when considered in connection with the accompanying drawings.

SUMMARY OF THE INVENTION

In general, the objects and advantages of the present invention are achieved by apparatus for drainage of a body cavity which includes a housing body generally sealed to the ambient atmosphere except for controlled venting as may be specifically provided, an elongated one-way valve mounted within the housing body, and a catheter supported by the housing body and extending outwardly therefrom. The apparatus thus described is intended to be used with a trocar, as will be hereinafter described. In accordance with the invention, the drainage apparatus and a trocar may be packaged in a sterile package to form a sterile kit for the drainage of a body cavity.

More particularly, the objects and advantages of the present invention are achieved by the following apparatus: A housing body is provided having portions which define an inlet chamber and a discharge chamber. The housing body portion defining the inlet chamber includes mounting means for supporting a catheter, preferably an intrapleural catheter, in sealed arrangement with the chamber. The catheter supported by the mounting means extends outwardly from the inlet chamber and is in fluid communication with the chamber. An inlet port is provided in the housing body portion defining the inlet chamber and is adapted to reversibly receive a trocar and is positioned to enable at least a portion of the trocar to pass through the inlet chamber and the catheter. The inlet port is adapted to seal the inlet chamber from the ambient atmosphere in the absence or presence of the trocar.

The apparatus includes a one-way elongated valve mounted in the housing body which couples in fluid communication the inlet chamber with the discharge chamber, so as to permit the passage of fluid between the chambers only through the valve. The valve can be substantially as described in Heimlich U.S. Pat. No. 3,463,159, and can be formed of a sleeve of substantially resilient fluid-impervious material, for example of latex rubber, or, preferably, of urethane or silicone elastomer. The sleeve has its inlet end held open and in communication with the inlet chamber, while its normally closed outlet end resides in the discharge chamber. The valve is normally held closed along a substantial length of the sleeve by the substantial resilience of the sleeve material, and is adapted to progressively open and close to permit the irreversible passage of drainage material passing therethrough from its inlet end to its outlet end.

In the use of the apparatus of the present invention, a trocar having an external diameter almost as large as the internal diameter of the catheter portion of the apparatus is inserted through the inlet port of the inlet chamber and through the catheter supported by the mounting means in one wall of the inlet chamber. The trocar end supporting the outermost end of the catheter, with the remainder of the apparatus suppported by the trocar, is inserted into the body cavity. Following insertion, the trocar is removed from the catheter, while leaving the end and at least the portion of the catheter adjacent thereto in the body cavity, and withdrawing the trocar from at least a substantial portion of the inlet chamber to provide communication from the catheter to the inlet chamber and the one-way valve. Preferably, the trocar is completely removed from the inlet chamber and the inlet port, and hence the apparatus, so as to avoid accidental reinsertion of the trocar or manipulation of the apparatus by accidental movement of the trocar. Upon removal of the trocar from the inlet port, the inlet port provides a seal to the ambient atmosphere. Fluids and other materials to be drained from the body cavity can now flow through the catheter into the inlet chamber and pass through the one-way elongated valve and into the discharge chamber where it is prevented from reentering the catheter and the body cavity by the presence of the one-way valve.

It can be seen that the apparatus of the present invention is most particularly adapted for insertion into the chest cavity in the area of the lungs, for the purpose of draining air and other fluids, as well as blood clots, particles and the like therefrom.

The apparatus of the present invention can further include on the exterior surface of the housing body portion defining the inlet chamber which includes the mounting means for supporting the catheter, a material which is adapted to adhere to the exterior of the body having the body cavity to be drained. Most preferably a self-adhesive strip is positioned on the described housing body portion defining the inlet chamber, and has a protective release sheet, which may be removed prior to insertion of the catheter into the body cavity to be drained. Upon insertion of the catheter, the adhesive strip adheres to the skin of the patient surrounding the opening formed by the trocar and catheter to support the apparatus thereon and to support the catheter within the body cavity upon the removal of the trocar from the inlet chamber and catheter.

Additionally, or in place of the adhesive strip positioned on the housing body portion, tape means can be provided extending from the housing body for releasably securing the apparatus to the skin of the patient adjacent the area in which the catheter of the apparatus is inserted. Preferably, the tape means comprises a plurality of tapes which are at least partially adhesive to adhere to the skin of the patient. Alternatively, the tape means can be a plurality of straps optionally with buckles, which can be used to tie or strap the housing body to the patient.

The apparatus of the present invention can be conveniently formed of relatively few parts by having as the housing body portion defining the inlet chamber a substantially solid body having one or more bores therein forming the inlet chamber. The substantially solid body can be formed of any rigid polymeric material, for example an acrylic polymer or polystyrene. The housing body portion can include a first bore extending therethrough in fluid communication with the catheter and the inlet port and is adapted to reversibly receive the trocar for passage through the bore from the inlet port to and through the catheter supported by the mounting means and extending outwardly from the inlet chamber. The substantially solid body preferably further includes means for mounting the one-way elongated valve thereto, for example, by having an annular shoulder, preferably of an oval shape, to which the inlet end of the sleeve of the valve can be secured. The substantially solid body preferably includes a second bore therein in fluid communication with the first bore and extending to the outside of the body and in fluid communication with the inlet end of the sleeve of the one-way valve. Most preferably, the portion of the second bore extending to the outside of the body is surrounded by the annular, preferably oval, shoulder to which the inlet end of the sleeve of the valve is mounted.

The mounting means for supporting the catheter in the housing body portion defining the inlet chamber can simply be a recess of the first bore into which the catheter can be molded, or can comprise a cannula sealingly affixed, for example by an adhesive, such as an epoxy adhesive, into a recess formed about the end of the first bore. The catheter can be sealed to the cannula, for example, through the use of an adhesive, such as an epoxy adhesive, or can be swaged to the cannula.

The discharge chamber of the apparatus can be formed of a molded, open topped, hollow housing body portion defining the chamber. The housing body portion is preferably fomred of a polymeric material, such as the material of which the housing body portion defining the inlet chamber is formed. The several wall segments forming the housing body portion defining the discharge chamber preferably is formed with at least one wall, and most preferably the wall which extends from the surface of the housing body portion defining the inlet chamber which includes the mounting means for supporting the catheter, which is angled inwardly at the lower portion thereof, so as to provide clearance between the body of the patient and the wall of the discharge chamber. As will be hereafter described, the discharge chamber of the apparatus preferably includes hydrophobic filter means, and by placing the filter means on, and the ports therefor in, the angled wall, clearance is provided between the patient and the ports or vents and filter means. If the wall containing or supporting the filter means and vents or ports is another wall of the discharge chamber, clearance is normally provided between that wall and any clothing or materials placed over the apparatus and the patient, and that wall may or may not be angled as desired.

In another embodiment of the invention, the housing body of the apparatus defining the inlet chamber can be formed of several integral walls and separable walls snap fitted thereto. Particularly, the housing body defining the inlet chamber can be an open-faced enclosure having back, side, top and bottom walls, and a separable face wall adapted to be snap fitted to the enclosure in fluid-sealing relation. The face wall can include the mounting means and the cathheter supported by the mounting means. The back wall of the enclosure can include the inlet port, while the bottom wall can define an aperture therein adapted to receive the inlet end of the sleeve of the one-way elongated valve. The back, side, top and bottom walls defining the enclosure are preferably integral with each other.

The apparatus in the embodiment preferably is formed with substantially flexible bellows-type means for supporting the inlet chamber and the discharge chamber in separated relation in which the inlet end of the sleeve of the one-way elongated valve is supported in sealed relation so as to communicate the inlet chamber with the discharge chamber through the valve. The apparatus can further include collar means positioned within the bellows-type means, for receiving the inlet end of the sleeve of the one-way valve, which can be turned about the collar means, and for sealing the inlet end of the sleeve thereagainst between the collar means and a portion of the interior surface of the bellows-type means. By having the bellows-type means formed of a resilient material and sized to closely fit the collar means, the turned portion of the sleeve of the valve may be pressed against the collar means and prevent the passage of fluid between the end of the sleeve and the collar means. The collar means can also include on its exterior portion ridges and recesses substantially conforming to the interior surface of the bellows-type means to assist in pressing and maintaining the inlet end of the sleeve of the valve turned about the collar means in sealed relation therebetween.

The inlet port of the inlet chamber of the apparatus, as in the previously described embodiment, further includes sealing means, including displaceable sealing material, positioned within the inlet chamber, for sealing the apparatus and the inlet port against the ambient atmosphere in the absence and upon insertion and withdrawal of a trocar with respect to the inlet chamber and the inlet port. At least a portion of the sealing means can be in axial alignment and in communication with the inlet port and at least a portion of the wall having the mounting means for supporting the catheter extending into the inlet chamber, whereby the portion of the said wall is supported in axial alignment with the inlet port in the absence of and upon withdrawal of a trocar from the inlet chamber.

The discharge chamber of the apparatus preferably includes hydrophobic filter means in communcation therewith. The hydrophobic filter means can comprise an elongated filter member mounted along on wall of the discharge chamber, and more preferably, the said wall can be formed with a plurality of ports with the elongated filter member positioned exteriorly of the wall, and the wall additionally including a cover member adapted to tightly fit to the wall to support the elongated filter member therebetween. In one form of the apparatus the cover member may include a plurality of ports open to the ambient atmosphere, whereby the discarge chamber is in communication with the ambient atmosphere only through the filter member. In another embodiment of the invention, the cover member or a wall of the housing can include a port connectable to drainage collection means or to suction means for applying suction to the discharge chamber of the apparatus through the filter member or through the wall. Preferably the filter means is positioned above the port, and hence above the expected level of liquid in the discharge chamber, where the port is included.

DETAILED DESCRIPTION OF PREFERRED EMBODIMENTS

Referring to the drawings, the numeral 10 designates generally intrapleural catheter apparatus in accordance with the present invention. Apparatus 10 includes a housing body 11 defining an inlet chamber 12 and a discharge chamber 13. For illustration purposes, apparatus 10 is shown with a trocar 14, it being understood that trocar 14 need not be considered a part of the apparatus, although it is used in connection with the apparatus, and is a member of the kit of the present invention, as will be hereinafter described.

In one preferred embodiment, as illustrated in FIGS. 1-4, housing body 11 includes a first portion 15 defining inlet chamber 12 and a second portion 16 defining discharge chamber 13. In this embodiment, housing body portion 15 comprises a substantially solid body, for example, a rigid acrylic polymer. Portion 15 includes a first bore 17 extending through portion 15. Bore 17 is enlarged at one end to form a recess 18 into which a cannula 19 is sealingly affixed, for example, by an epoxy adhesive. Cannula 19 functions as mounting means for a catheter 20 supported thereby. Catheter 20 is adhesively sealed to cannula 19 so as to firmly support the catheter and prevent the passage of air or other fluids from the outside of housing body 11 to inlet chamber 12.

Figure 1:
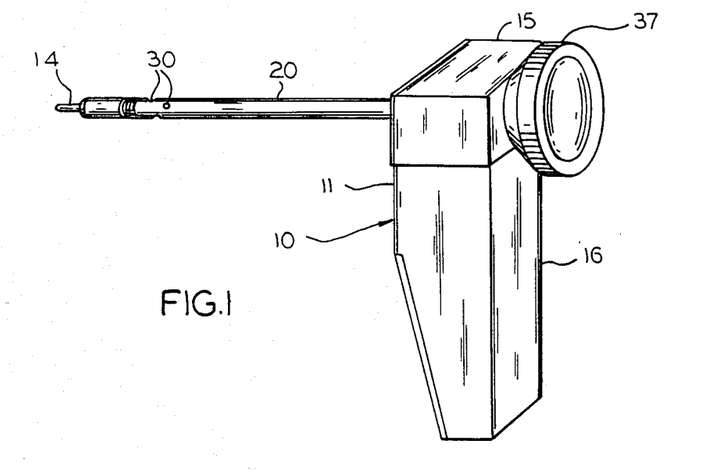
FIG. 1 is a perspective view of apparatus in accordance with the present invention with a trocar inserted into the inlet chamber and the catheter.
Figures 2, 3, 3A:
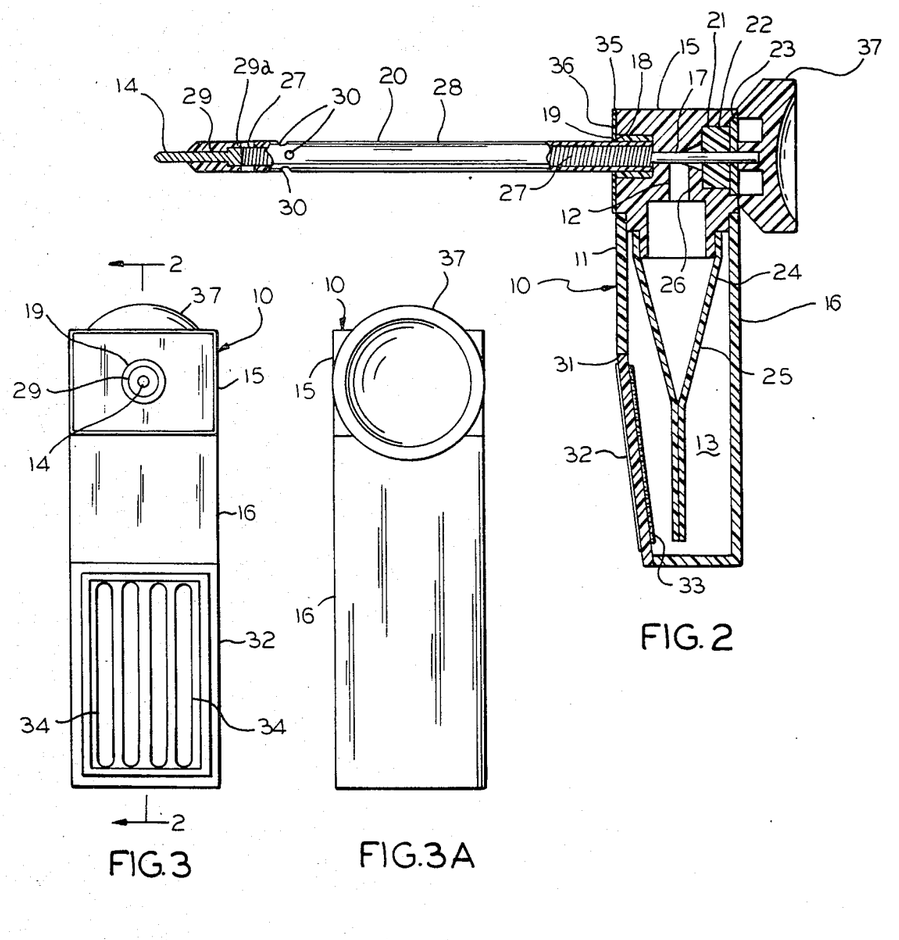
FIG. 2 is a partially sectional view of the apparatus shown in FIG. 1 taken along lines 2—2 of FIG. 3, with a trocar inserted.
FIG. 3 is a front elevational view of the apparatus shown in FIG. 1 with a trocar inserted.
FIG. 3A is a rear elevational view of the same apparatus.

The other end of bore 17 is enlarged to form a recess 21 which, together with displaceable, flexible sealing material 22 residing in recess 21, constitutes an inlet port through which trocar 14 can be inserted and withdrawn. Sealing material 22 can be a natural latex disc through which an opening is formed by the insertion of the trocar, and which seals itself upon withdrawal of the trocar. Sealing material 22 is held in place by a polymeric disc or washer 23, which is formed of the same material as body portion 15 and is sealed to portion 15 by welding by ultrasonic waves or by an adhesive, such as an epoxy adhesive. Preferably, disc or washer 23 is pressure or compression sealed to portion 15, which can be obtained, for example by welding washer 23 to portion 15 by ultrasonic waves. Bore 17 may have a tapered, conical shape inwardly of recess 21 so that the end of trocar 14 will be cammed so as to be axially centered in bore 17 upon insertion into the bore.

Housing body portion 15 in this embodiment, further includes an external shoulder 24 extending within housing body 11 about which the inlet end of the sleeve of a one-way elongated valve 25 can be secured. As heretofore noted, valve 25 can be substantially as described in Heimlich U.S. Pat. No. 3,463,159, and can be formed of a sleeve of substantially resilient fluid-impervious material, preferably of urthane or silicone elastomer. Shoulder 24 is preferably an annular shoulder having an oval shape, about which the inlet end of the sleeve is secured by tightly fitting about the shoulder. Alternatively, a band of heat-shrinkable elastomer (not shown in FIGS. 2 and 4) can be placed about the portion of the inlet end of valve 25 positioned about shoulder 24 and heat shrunk to hold the inlet end of the valve to the shoulder. In this manner, the inlet end of the sleeve of valve 25 is held open within housing body 16. A second bore 26 is formed in housing body portion 15 which intersects and is in fluid communication with first bore 17 and extends to the outside of body portion 15 so as to be in fluid communication with the inlet end of the sleeve of valve 25. Bore 26 in body portion 15 can be enlarged adjacent its end in communication with valve 25 to facilitate the passage of fluids from bore 17 to the inlet end of valve 25. In this embodiment, bore 17 and bore 26, together, comprise the inlet chamber of the apparatus heretofore described.

Catheter 20, in this embodiment, is preferably formed of a stainless steel spring as a core 27 covered with an elastomer 28, which preferrably is a polyurethane coating molded thereto. The tip 29 preferably is of resilient polymer, such as of urethane or silicone polymer, and is bonded to the end of spring core 27.

The end of tip 29 is open to permit the end of trocar 14 to pass therethrough. Tip 29 is spaced from the end of coating 28 so as to provide an annular aperture spaced from the end of catheter 20, i.e., adjacent the tip end thereof, to facilitate assembly of catheter, and the annular aperture is filed with clear adhesive, such as epoxy adhesive. Elastomer covering 28 includes a plurality of ports 30, spaced from each other, adjacent filled aperture 27. Following insertion of the catheter into a body cavity to be drained and removal of trocar 14, the ports 30 in coating 28 permit fluids and other drainage material from the body cavity to pass through the thus exposed coils of core 27 beneath the ports 30, into the interior passage of catheter 20 formerly occupied by trocar 14 and into bores 17 and 26 to the inlet end of the sleeve of one-way valve 25.

Housing body portion 16 (hereafter "housing 16"), defining discharge chamber 13 is a molded, open topped, housing defining the discharge chamber 13. Housing 16 can be molded of the same material as housing body portion 15. As best shown in FIG. 2 one-way elongated valve 25 freely resides within housing 16 which is adapted to receive drainage material passing from the outlet end of the valve. Housing 16 includes an opening or port 31 which is adapted to be closed by a cover 32 supporting an elongated hydrophobic filter 33 which can be affixed to the cover with an adhesive, such as an epoxy adhesive. Cover 32 defines a plurality of ports or vents 34 which permits gaseous fluids, including air, to pass through filter 33 and through vents 34 to the atmosphere. In addition, cover 32 tightly fits to the edges of port 31, and can be adhesively affixed thereto, to provide an air-tight seal of the cover to the port.

In the embodiment shown, housing 16 is provided with a truncated or angled portion in the area forming port 31, and cover 32 is adapted to assume the angle provided by port 31, to cause a tapered space between the body of the patient and the vents 34 of cover 32 to permit gaseous fluids to escape from discharge chamber 13 when apparatus 10 is installed to the body of the patient. Alternatively, port 31, and consequently cover 32 and filter 33, can be formed in another portion of housing 16 so that the filter and cover will face in another direction so as not to be blocked by the body of the patient upon installation of the apparatus.

Housing body portion 15, and particularly the surface thereof from which catheter 20 extends includes on its exterior surface a self adhesive strip 35 which is adapted to adhere to the exterior of the body of the patient having the body cavity to be drained. Adhesive strip 35 is covered by a protective release sheet 36 which is removed prior to insertion of catheter 20 into the body cavity to be drained.

Figures 4, 5:
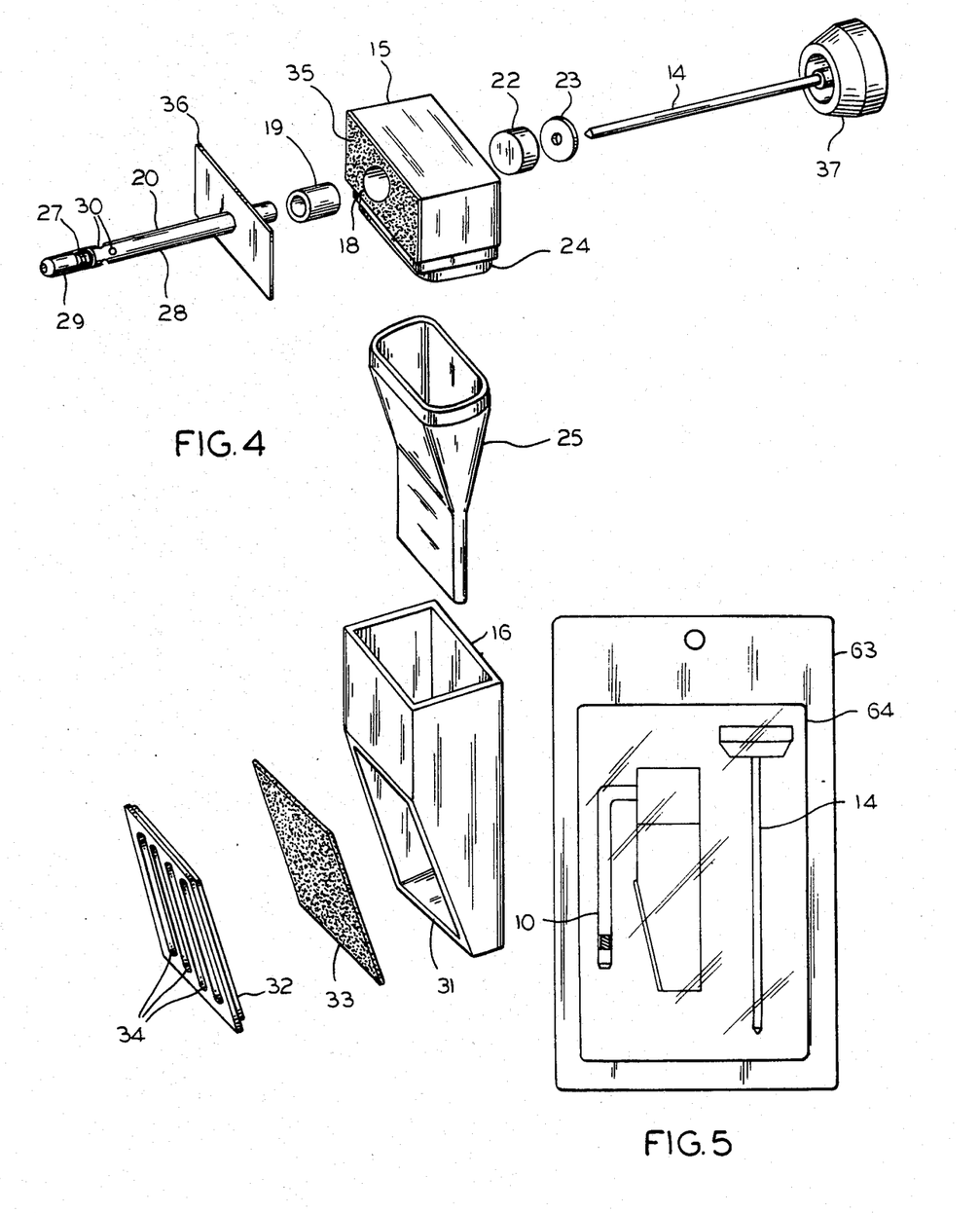
FIG. 4 is an exploded, perspective view of the apparatus shown in FIGS. 1-3 and FIG. 3A.
FIG. 5 is a front elevational view of a kit in accordance with the present invention.

The catheter apparatus thus described can be readily assembled, as particularly shown in FIG. 4. In such assembly, the inlet port can be established by inserting sealing material 22 into recess 21 and covering the sealing material with disc or washer 23 and pressure sealing the same within recess 21 by welding with ultrasonic waves. Adhesive strip 35 can be applied to the surface of housing body portion 15 having recess 18, and release sheet 36 can be placed over adhesive strip 35. Cannula 19 is fitted within recess 18 and sealed thereto. Catheter 20 is desirably preformed with covering 28 bonded to stainless steel spring core 27, tip 29 bonded to the end of core 27, and the annular space about core 27 between the end of covering 28 and tip 29 filled with a clear adhesive, such as an epoxy adhesive. with its shoulder 29a against the end of core 27. The opposite end of catheter 20 can be inserted into and sealed to cannula 19 as heretofore described. The inlet end of one-way elongated valve 25 is fitted to shoulder 24 of body 15, and if desired, sealed thereto by means of heat shrinking a band of heat-shrinkable material (not shown) placed about the inlet end of the sleeve of valve 25. Filter 33 can be affixed to cover 32, and cover 32 affixed to port 31 of housing 16 to complete the latter. Housing 16 can then be placed about the sleeve of valve 25 and can be forced upwardly to surround the bottom or a step-shaped shoulder of housing body 15 in a fluid tight manner, or adhesively affixed thereto, to complete the apparatus. Trocar 14 is conveniently provided with a handle 37 which can be molded or affixed thereto with an epoxy adhesive.

Figures 6, 7:
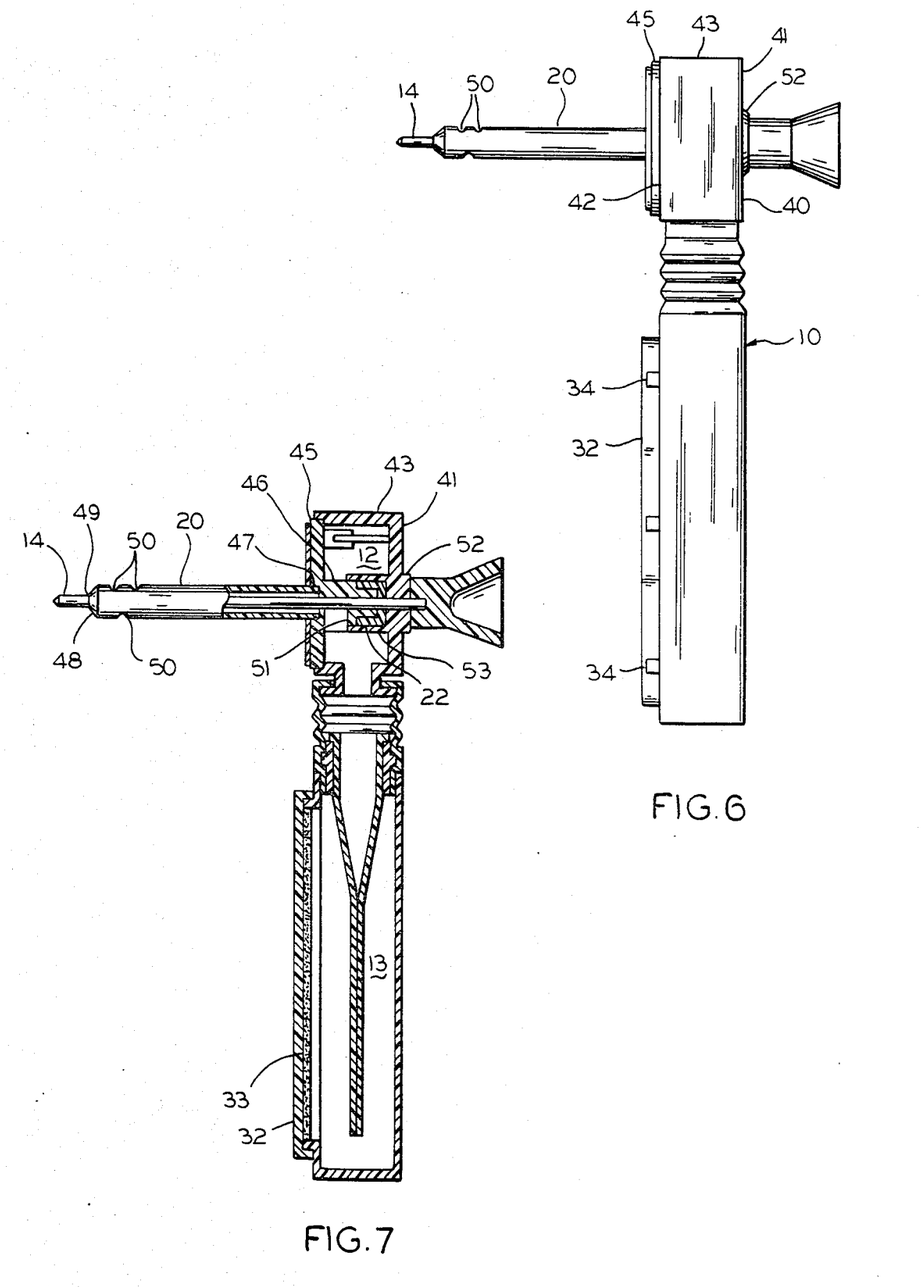
FIG. 6 is a side elevational view of another embodiment of apparatus in accordance with the present invention with a trocar inserted into the inlet chamber and the catheter.
FIG. 7 is a partially sectional side elevational view of the apparatus shown in FIG. 6.
Figures 8, 9:
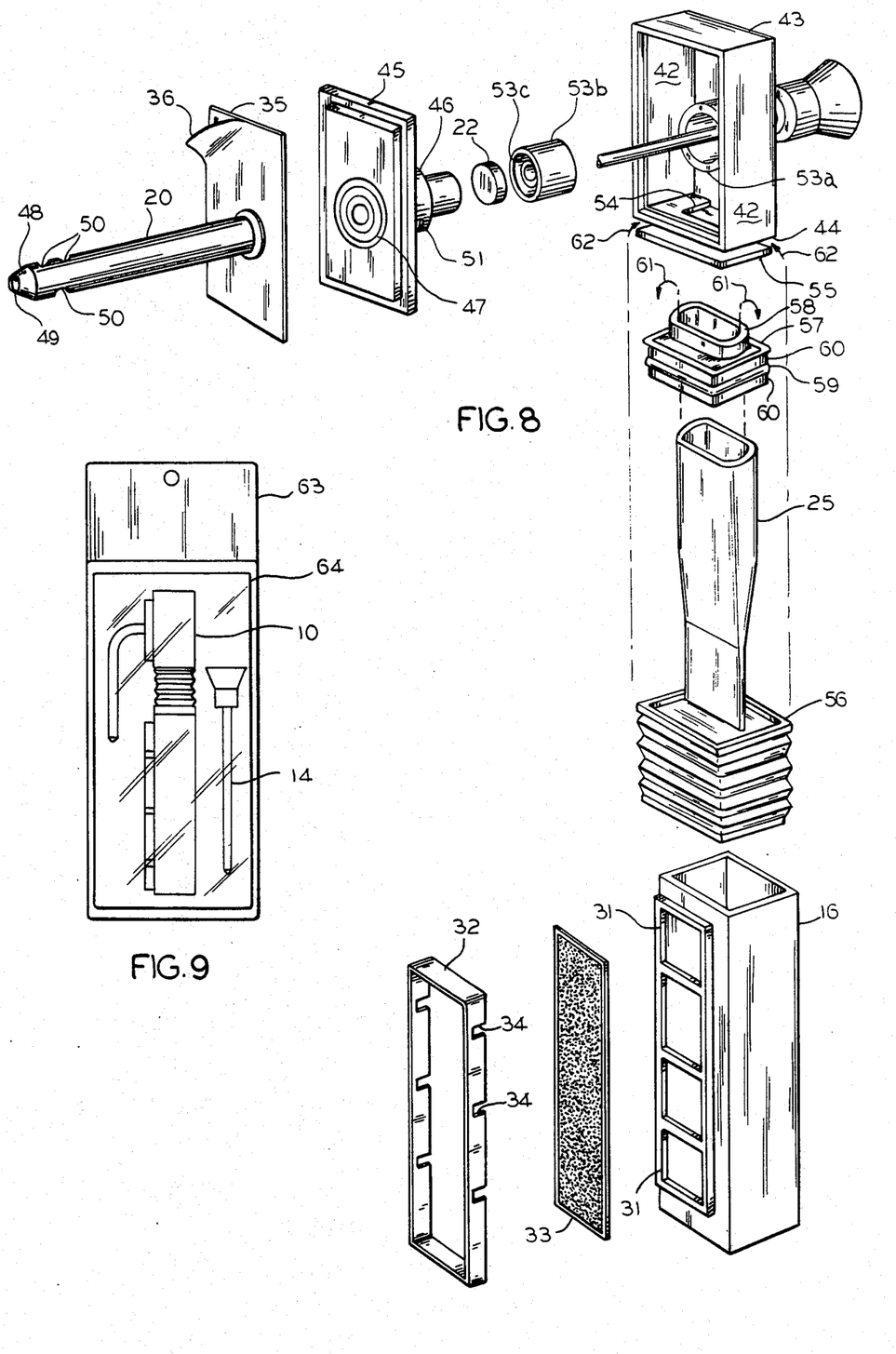
FIG. 8 is an exploded, perspective view of the apparatus shown in FIGS. 6 and 7.
FIG. 9 is a front elevational view of a kit which includes the apparatus shown in FIGS. 6-8.

Another embodiment of the apparatus of the present invention is shown in FIGS. 6–8, in which the same reference numerals have been used for elements which are substantially the same as those in the embodiment illustrated in FIGS. 1–4.

Apparatus 10 in this embodiment includes an upper housing 40, constituting inlet chamber 12, defined by back wall 41, side walls 42, top wall 43 and bottom wall 44, which are integral with each other. A face or front wall 45 snap-fits into the front of the opening formed by side walls 42, top wall 43, and bottom wall 44 to complete inlet chamber 12.

Face wall 45 of inlet chamber 12 includes an aperture formed therein surrounded by a thickened portion 46 having an annular, outwardly facing recess 47 which serves as mounting means for the catheter 20, portion 46 extending inwardly of wall 45. Catheter 20 is mounted in the recess 47 of portion 46 and extends outwardly from wall 45. Catheter 20 has an outer end 48 having a trocar receiving aperture 49 and fluid receiving ports 50. Catheter 20 extends outwardly of wall 45 a sufficient distance so as to permit the outer end 48 and ports 50 to be positioned in a body cavity to be drained. Portion 46 includes an opening port 51 (FIG. 7) communicating with the interior of inlet chamber 12 and arranged to permit fluids and material drained from the body cavity by the catheter 20 to enter inlet chamber 12.

Back wall 41 includes thickened portion 52 which defines the inlet port for trocar 14. Portion 52 extends interiorly of the inlet chamber, with an annular portion 53 thereof extending concentrically with the path of trocar 14. Annular portion 53 is formed by an annular shoulder 53a integral with wall 45, and a cylindrical insert 53b of which fits snuggly within shoulder 53a in a fluid-sealed relation, as best shown in FIG. 8. Annular portion 53 includes an annular recess 53c adapted to support sealing material 22 for sealing the inlet port as described. The inlet port is axially aligned with the aperture in portion 46 of wall 45 and the path of trocar 14 to permit the tubular portion of trocar 14 to progressively and smoothly, reversibly pass through the inlet port, the aperture in portion 46 and catheter 20. Portion 46 of wall 45 extends into annular recess 53c of portion 53, although it does not contact the walls of the recess for ease of assembly of face wall 45 to integral walls 41–44. Flexible sealing material 22, encircled by recess 53c, serves as the sealing means described above for sealing the inlet port in the absence of trocar 14 and for sealing the inlet port to trocar 14 when the latter is present therein or during its passage through or withdrawal from chamber 12. Sealing material 22 further functions to seal portion 46 at its extention into recess 53c.

Bottom wall 44 includes an aperture 54 formed therein and an annular, outwardly extending and depending integral L-shaped flange 55. Suspended beneath bottom wall 44 by a substantially flexible bellows-shaped member 56, is discharge chamber 13 separated from inlet chamber 12. Discharge chamber 13 is defined by an upwardly open housing 16 as in the previously described embodiment. A collar 57 is positioned within bellows-shaped member 56 beneath and separated from bottom wall 44. Collar 57 is formed with a vertical aperture adapted to receive the upper, open end of a one-way elongated valve 25 which extends into housing 16 forming discharge chamber 13. The aperture and the upper portion of collar 57 which comprises a raised shoulder 58 is formed substantially to the shape of the upper, open end of valve 25, which is turned about shoulder 58. The bellows-shaped member 46 is formed of a resilient material and is sized to closely fit the exterior sides of collar 57 and its shoulder 58. In addition, bellows-shaped member 56 is formed and shaped to closely fit to flange 55 of bottom wall 44 so as to maintain a firm, but flexible spaced relation between collar 57 and bottom wall 44 and maintain a sealed relation therebetween with respect to the ambient atmosphere. Collar 57 includes on its exterior portion ridges 59 and recesses 60 conforming to the interior surface of bellows-shaped member 56 to assist in pressing and maintaining the aforesaid spaced and sealed relation.

As heretofore described, housing 16 includes a wall formed with at least one port 31. Housing 16, as best shown in FIG. 8, includes a wall which is elongated and defines a plurality of the ports 31 which in this embodiment extend outwardly from housing 16. An elongated hydrophobic filter 33 is positioned against the portion of the wall which defines ports 31. A cover 32 defines a plurality of vents 34 positioned along the elongated sides of member 32. Cover 32 is adapted to tightly fit to the exterior of the wall and supports filter 33 therebetween. In addition, filter 33 is heat-sealed to the wall to prevent the discharge of gaseous fluids from discharge chamber 13, except through filter 33 and vents 34.

As in the previously described embodiment, housing body 11, and particularly wall 45 defining inlet chamber 12 includes on its exterior surface, a self-adhesive strip 35 covered by protective release sheet 36 which is removed prior to insertion of the catheter into the body cavity to be drained.

The catheter apparatus thus described can be readily assembled, as particularly shown in FIG. 8. In such assembly, the normally open end of the elongated one-way valve 25 can be inserted through the aperture in collar 57 and turned about shoulder 58 as shown by the path designated by arrows 61. Bellows-shaped member 56 can be slipped upwardly about valve 25 and positioned with its lower portion surrounding and holding collar 57 and the portion of valve 25 which is turned about shoulder 58 of the collar. In this position, bellows-shaped member 56 maintains valve 25 and collar 57 in fluid sealed relation to each other so that fluid materials will pass only through the valve. Bellows-shaped member 56 can then be placed about flange 55 of the bottom wall 44 of the upper housing 40 as shown by the path designated by arrows 62 to establish a spaced apart relation between the upper housing 40 defining inlet chamber 12 and valve 25 in collar 57. The inlet port can next be established by inserting insert 53b with sealing material 22 residing in recess 53c into the aperture defined by the cylindrical shoulder 53a. Wall 45 is snap fitted to the opening housing 40 formed by walls 41–44, with a portion of thickened portion 46 extending into recess 53c and contacting sealing material 22. Adhesive strip 35 can be applied to wall 45 and release sheet 46 in turn applied thereto, or the adhesive strip and the release sheet can be applied to wall 45 prior to its assembly to form the inlet chamber. Catheter 20 can be mounted to wall 45 through an aperture in release sheet 36 and adhesive strip 35 to complete the assembly of the upper portion of the apparatus. Filter 33 can be applied to cover 32 and heat sealed thereto if desired, and cover 32 applied to port 31 in housing 30 to assemble discharge chamber 13. Finally, housing portion 16 defining the said chamber can be forced upwardly to surround the bottom of bellows-shaped member 56 to complete the assembly of the apparatus.

The present invention includes the provision of a sterile kit particularly adapted for the drainage of a body cavity. As best shown in FIGS. 5 and 9, the sterile kit comprises a sealed package, such as a backing card 63 and transparent covering film 64 defining a sterile interior. Positioned therebetween in the sterile interior of the package are an intrapleural catheter apparatus 10 in accordance with the present invention and a trocar 14 including a handle 37. It is contemplated that both catheter apparatus 10 and trocar 14 are maintained in a sterile condition prior to packaging in the sterile kit, and that the kit can be conveniently assembled under sterile conditions by positioning apparatus 10 and trocar 14 on card 63. Following assembly, the kit remains sterile until film 64 is pierced or removed.

The utilization of the apparatus of the present invention will now be described. If the catheter apparatus 10 is supplied in the sterile kit, the apparatus is removed from the kit under sterile conditions. The trocar, being handled by its handle 37 is inserted through the inlet port of housing body 11 so that its end opposite handle 37 passes through inlet chamber 12 and catheter 20. As shown in FIGS. 1–3, 6 and 7, catheter 20 will be straightened and aligned by trocar 14 passing therethrough. With the end of trocar 14 opposite handle 37 extending through and beyond the end of catheter 20, the release sheet 36 is removed from the adhesive strip 35, and the end of trocar 14 is inserted into the body of the patient through the skin and underlying tissue into the body cavity to be drained. Upon full insertion of trocar 14 and catheter 20 therewith into the body cavity, self-adhesive strip 35 will adhere to the skin of the patient to maintain the catheter apparatus in place. Thereafter trocar 14 can be withdrawn by manipulation of handle 37. Upon withdrawal of trocar 14 from inlet chamber 12, the inlet port is sealed by sealing material 22. Fluid and other material from the body cavity to be drained can now pass through the aperture and/or ports 30, 50 of catheter 20 and pass therefrom through into inlet chamber 12 and the open end of valve 25. As heretofore described, fluids can progressively pass through valve 25 into discharge chamber 13. Gases, particularly air, are vented from discharge chamber 13 through hydrophobic filter member 33 and out through vents 34 formed in cover 32.

Figures 10, 11, 12:
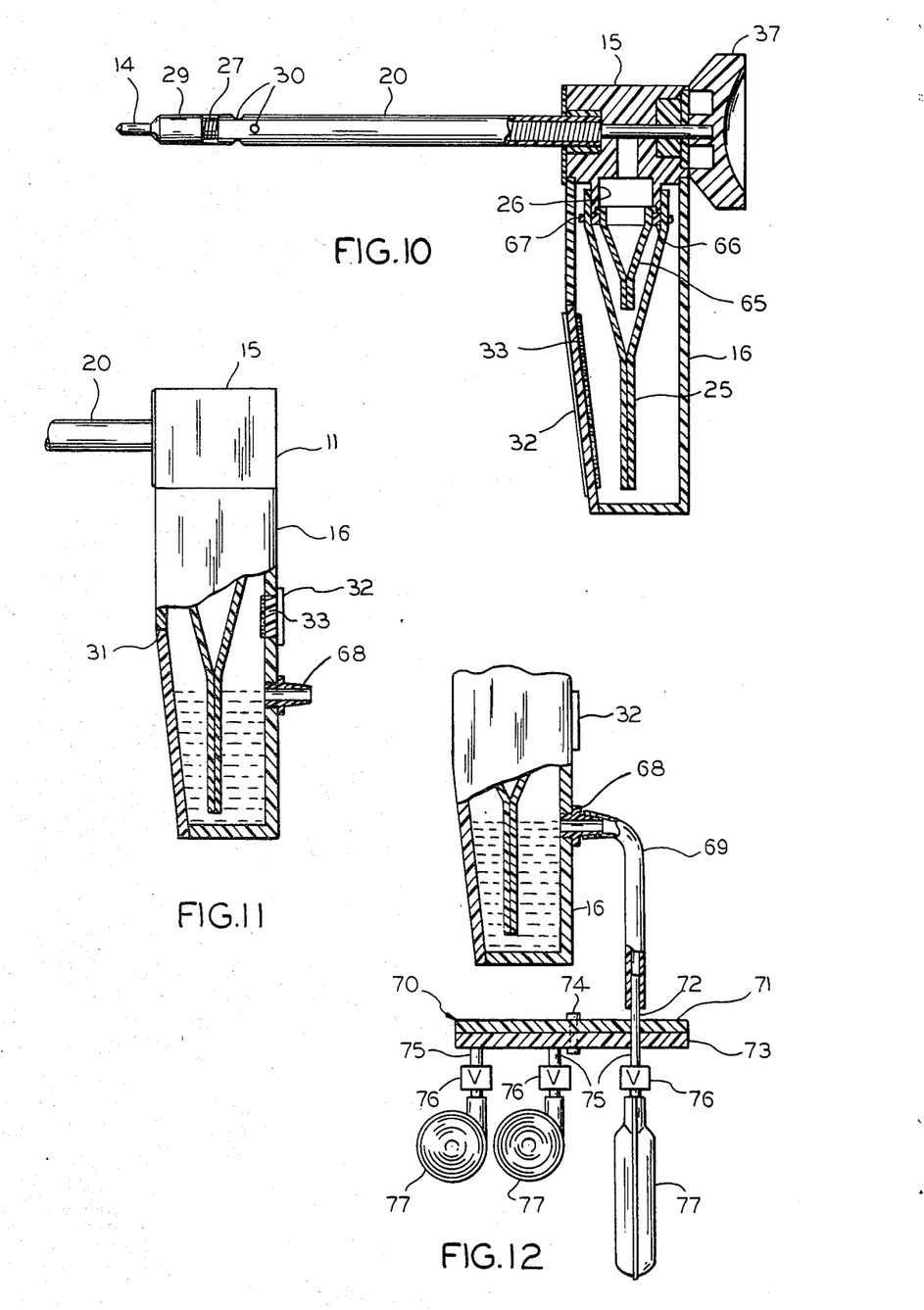
FIG. 10 is a partially sectional side elevational view of still another embodiment of the present invention with a trocar inserted into the inlet chamber and the catheter.
FIG. 11 is a fragmentary, partially sectional side elevational view of the apparatus in accordance with the present invention including a port for suction and/or drainage of the apparatus.
FIG. 12 is a fragmentary, partially sectional side elevational view of the apparatus shown in FIG. 11, with drainage collection apparatus.

The apparatus of the present invention can include an additional one-way valve, as illustrated in FIG. 10. The apparatus there shown is, in all major respects, identical to the apparatus in FIGS. 1–4, and like reference numerals have been utilized for similar elements. Additionally, a second one-way valve 65 is mounted to housing body portion 15 so as to be positioned between and in fluid communication with inlet chamber 12 and the inlet end of the sleeve of one-way elongated valve 25. As shown in the drawing, one-way valve 65 can be a duck-bill valve, such as those commercially available from Vernay Co., and particularly a duck-bill valve with a molded lip at its upper end. Valve 65 can be adhesively affixed to a disc or washer 66 of polymeric material, preferably the same material as body portion 15, and the subassembly of valve 65 and washer 66 adhesively sealed to the bottom of housing body 15 with the exposed lip of valve 65 fitting within the enlarged recess of bore 26. The outer annular perimeter of washer 66 preferably has substantially the same diameter as shoulder 24, so that upon assembly washer 66 becomes an extension of housing body 15 and shoulder 24. The open inlet end of valve 25 can be placed about washer 66 and shoulder 24, and thereafter a ring or band of rubber or heat shrinkable material 67 can be placed about the open, inlet end of the sleeve of valve 25, and if the latter, heat shrunk, to firmly affix and seal valve 25 to shoulder 24. The utilization of second valve 65 in conjunction with the apparatus of the present invention further enhances the utility of the apparatus to prevent the back flow of material if any material should remain in the inlet end of the sleeve of valve 25 or if any material should move in the reverse direction through valve 25.

The apparatus of the present invention can also include a port 68, which can be in the form of a nipple as shown in FIG. 11 for the purpose of applying suction or for draining discharge chamber 13. In providing port 68, it is preferable to modify housing body 11, and particularly housing 30 by moving the hydrophobic filter 33 and the cover 32 to another wall of housing 30 between the location of port 68 and the housing body 15 or upper housing 40 of the apparatus as shown. Port 31 is then closed by a solid wall which is sealed thereto as shown in the drawing. Furthermore, port 68 can be formed in cover 32, so that suction can be applied to discharge chamber 13 through filter 33, and thereby facilitate the drainage of fluids, and permit the drainage of small amounts of other materials such as small pieces of tissue, through the catheter apparatus in the same manner as fluids.

The apparatus of the present invention including port 68, can be utilized to collect drainage from the body cavity being drained, as illustrated FIG. 12. As shown, a conduit 69 is provided fitted or coupled to port 68 at one end and to drainage collection apparatus 70, at its other end. Apparatus 70 can comprise a first rotatable disc 71 having a tube 72 passing therethrough and extending upwardly to which conduit 69 is coupled. A second disc 73 is rotatably mounted to disc 71 by means of a fastener, such as rivet 74. Disc 73 has a plurality of tubes 75 circumferentially spaced about disc 73 which are each connected to a valve 76 and the valve in turn connected to drainage receptacles such as bags 77, which may be initially rolled, as shown. As tubes 75 are circumferentially spaced in disc 73 at the same radius from the center as tube 72 is spaced from the center of disc 71, each of tubes 75, and hence valves 76, and collection receptacles 77 can be selectively spaced under and in communication with tube 72 upon rotation of disc 73. In this manner, each of collection bags 77 can be sequentially filled with drainage material, and can be removed upon closing of the respective valve 76 for analysis of the material, or for disposal, or for another purpose.

Alternatively, to provide drainage collection apparatus, a known collection device, such as the medical suction device described in U.S. Pat. No. 4,404,924 can be connected to port 68 to provide collection of the drainage material from discharge chamber 13 of the present apparatus as well as remote indication of the suction being applied to the apparatus.

Various changes coming within the spirit of the invention may suggest themselves to those skilled in the art; hence, the invention is not limited to the specific embodiments shown or described and uses mentioned, but the same is intended to be merely exemplary, the scope of the invention being limited only by the appended claims.

We claim:

1. Apparatus for drainage of a body cavity, comprising:

a housing body having portions defining an inlet chamber and a discharge chamber;

said housing body portion defining said inlet chamber having mounting means for supporting a catheter in sealed arrangement therewith and in fluid communication with said inlet chamber;

a catheter supported by said mounting means and extending outwardly from said inlet chamber, said catheter being in fluid communication with said inlet chamber;

an inlet port in said housing body portion defining said inlet chamber having inlet port sealing means which is adapted to reversibly receive a trocar and enable at least a portion of a trocar to pass through said inlet chamber and said catheter, and said inlet port sealing means for sealing said chamber against the ambient atmosphere in the absence of a trocar, and upon insertion and withdrawal of a trocar from at least said catheter to seal said inlet chamber from the ambient atmosphere;

a one-way valve mounted in said housing body and coupling said inlet chamber with said discharge chamber so as to prevent the passage of fluid between said chambers except through said valve, said valve having its inlet end in communication with said inlet chamber, said valve having its outlet end in fluid communication with said discharge chamber, said valve being adapted to permit passage of drainage material passing therethrough from its inlet end to its outlet end.

2. The apparatus as defined in claim 1 wherein the housing body portion defining said inlet chamber comprises a substantially solid body having a first bore extending therethrough and in fluid communication with said catheter and said inlet port and adapted to reversibly receive a trocar for passage therethrough, said substantially solid body having means for mounting the one-way valve thereto within said housing body, and said substantially solid body having a second bore therein in fluid communication with said first bore and in fluid communication with the inlet end of said one-way valve.

3. The apparatus as defined in claim 2 wherein said mounting means for supporting the catheter in said housing body portion defining said inlet chamber comprises a cannula sealingly affixed in a first end portion of the substantially solid body defining the first bore and supporting the catheter outwardly extending therefrom, the catheter being secured to said cannula.

4. The apparatus as defined in claim 1 wherein the housing body portion defining said inlet chamber comprises an open-faced enclosure having back, side, top and bottom walls, and a separable face wall adapted to be secured to said enclosure in fluid-sealing relation thereto, said face wall including said mounting means and said catheter supported thereby, said back wall having said inlet port, and said bottom wall defining an aperture therein adapted for fluid communication with said one-way valve.

5. The apparatus defined in claim 4 wherein said back, side, top and bottom walls are integral with each other.

6. The apparatus as defined in claim 1 wherein said inlet chamber and said discharge chamber are separated by a substantially flexible bellows-shaped member in which the inlet end of said one-way valve is supported in sealed relation communicating said inlet chamber with said discharge chamber.

7. The apparatus as defined in claim 1 wherein said sealing means includes displaceable sealing material positioned within said inlet chamber for sealing said chamber against the ambient atmosphere in the absence of and upon insertion and withdrawal of a trocar with respect to said inlet chamber and said inlet port.

8. The apparatus as defined in claim 1 wherein said discharge chamber includes hydrophobic filter means in communication therewith for filtering gaseous fluids from said discharge chamber.

9. The apparatus as defined in claim 8, wherein said hydrophobic filter means comprises an elongated filter member mounted along one wall of the housing body portion defining said discharge chamber.

10. The apparatus as defined in claim 9, wherein said wall of the housing body portion defining said discharge chamber is formed with at least one port, said elongated filter member is positioned exteriorly of said wall and said port, and said wall includes a cover member adapted to support said elongated filter member between said cover member and said wall.

11. The apparatus as defined in claim 10, wherein said cover member includes at least one port open to the ambient atmosphere, whereby said discharge chamber is in communication with the ambient atmosphere only through said filter.

12. The apparatus as defined in claim 10, wherein said cover member includes a port connectable to suction means whereby suction can be applied to the discharge chamber of said apparatus through said filter.

13. The apparatus as defined in claim 9 wherein said housing body portion defining said discharge chamber includes a port connectable to suction means for applying suction to the discharge chamber of said apparatus to assist in drainage.

14. The apparatus as defined in claim 9 wherein said housing body portion defining said discharge chamber includes a port connectable to drainage collection means for receiving drainage from said discharge chamber.

15. The apparatus as defined in claim 14 including drainage collection means comprising a plurality of collection containers, distributing means for selectively distributing drainage received from said discharge chamber to each of said plurality of collection containers, and a conduit leading from said port to said distributing means for conducting drainage from said port to said distributing means.

16. The apparatus as defined in claim 1 wherein said catheter comprises a spring core covered by a elastomeric coating.

17. The apparatus as defined in claim 16 wherein the said catheter includes at least one aperture in the coating thereof adjacent its tip end, through which materials from the body cavity are adapted to pass to and through the core thereof into the catheter upon the catheter being inserted into the body cavity to be drained.

18. The apparatus as defined in claim 1, wherein said oneway valve is a one-way elongated valve being formed of a sleeve of substantially resilient, fluid-impervious material and having its inlet end held open, said valve being normally held closed along a substantial length of the sleeve by the substantial resilience of the material of said sleeve and adapted to progressively open and close to permit the irreversible passage of drainage material passing therethrough from its inlet end to its outlet end.

19. The apparatus as defined in claim 18, wherein said inlet chamber and said discharge chamber are separated by a substantially flexible bellows-shaped member in which the inlet end of the sleeve of said one-way elongated valve is supported in sealed relation communicating said inlet chamber with said discharge chamber, and including collar means positioned within said bellows-shaped member for receiving the inlet end of the sleeve of said one-way elongated valve.

20. The apparatus as defined in claim 19 wherein said collar means comprises a collar having a shoulder adapted to receive the inlet end of the sleeve of said one-way valve with the inlet end of said sleeve through said collar the inlet end of said sleeve being turned about said shoulder, and sealed thereagainst by a portion of the interior surface of the bellows-shaped member pressing thereagainst and preventing the passage of fluid between said inlet end of the sleeve of said valve and said collar.

21. The apparatus as defined in claim 20 wherein said collar includes an exterior portion having ridges and recesses conforming to the interior surface of said bellows-shaped member for maintaining a sealed relation therebetween.

22. The apparatus as defined in claim 18 including a second one-way valve mounted in said housing body between and in fluid communication with said inlet chamber and the inlet end of the sleeve of said first one-way elongated valve so as to prevent the passage of fluid between said inlet chamber and said first one-way elongated valve except through said second valve.

23. The apparatus as defined in claim 22 wherein said second one-way valve is formed of a sleeve of substantially resilient, fluid-impervious material and is positioned within and axially aligned with the held open inlet of the sleeve of said first one-way elongated valve, and said second one-way valve having its inlet end held open and in communication with said inlet chamber.

24. The apparatus as defined in claim 18, wherein said sealing means includes displaceable sealing material positioned within said inlet chamber for sealing said chamber against the ambient atmosphere in the absence of and upon insertion and withdrawal of a trocar with respect to said inlet chamber and said inlet port.

25. The apparatus as defined in claim 18, wherein said discharge chamber includes hydrophobic filter means in communication therewith for filtering gaseous fluids from said discharge chamber.

26. The apparatus as defined in claim 25, wherein said hydrophobic filter means comprises an elongated filter member mounted along one wall of the housing body portion defining said discharge chamber, said wall being formed with at least one port and including a cover member adapted to support said elongated filter member positioned exteriorly of said wall and said port, said wall including a cover member adapted to support said elongated filter member between said cover member and said wall.

27. The apparatus as defined in claim 26, wherein said cover member includes at least one port open to the ambient atmosphere, whereby said discharge chamber is in communication with the ambient atmosphere only through said filter.

28. The apparatus as defined in claim 25, wherein said housing body portion defining said discharge chamber includes a port connectable to suction means for applying suction to the discharge chamber of said apparatus to assist in drainage.

29. The apparatus as defined in claim 25, wherein said housing body portion defining said discharge chamber includes a port connectable to drainage collection means for receiving discharge from said discharge chamber.

30. The apparatus as defined in claim 29 including drainage collection means comprising a plurality of collection containers, distributing means for selectively distributing drainage received from said discharge chamber to each of said plurality of collection containers, and a conduit leading from said port to said distributing means for conducting drainage from said port to said distributing means.

31. A sterile kit for the drainage of a body cavity comprising:
a sealed package the interior of which is sterile;
apparatus for drainage of a body cavity positioned within the interior of said package, comprising:
a housing body having portions defining an inlet chamber and a discharge chamber;
said housing body portion defining said inlet chamber having mounting means for supporting a catheter in sealed arrangement therewith and in fluid communication with said inlet chamber;
a catheter supported by said mounting means and extending outwardly from said inlet chamber, said catheter being in fluid communication with said inlet chamber;
an inlet port in said housing body portion defining said inlet chamber having inlet port sealing means which is adapted to reversibly receive a trocar and enable at least a portion of the trocar to pass through said inlet chamber and said catheter, and said inlet port sealing means for sealing said chamber against the ambient atmosphere in the absence of and upon insertion and withdrawal of a trocar from at least said catheter
a one-way valve mounted in said housing body and coupling said inlet chamber with said discharge chamber so as to prevent the passage of fluid between said chambers except through said valve, said valve having its inlet end in communication with said inlet chamber, said valve having its outlet end in fluid communication with said discharge chamber, said valve being adapted to permit the irreversible passage of drainage material passing therethrough from its inlet end to its outlet end; and
a trocar positioned within the interior of said package having a portion adapted upon utilization of the apparatus to be inserted into said inlet chamber through said inlet port and through said catheter into a body cavity to be drained, and to be withdrawn from said body cavity, said catheter and said inlet chamber, while leaving the catheter in communication with said body cavity, while the portion in the inlet chamber and inlet port is sealed against the ambient atmosphere by a said sealing means.

32. The sterile kit as defined in claim 31, wherein said one-way valve mounted in said housing body of said apparatus is a one-way elongated valve being formed of a sleeve of substantially resilient, fluid impervious material, having its inlet and held open, said valve being normally held closed along a substantial length of the sleeve by the substantial resilience of the material of said sleeve and adapted to progressively open and close to permit the irreversable passage of draining material passing therethrough.

33. The sterile kit as defined in claim 32, wherein the apparatus for drainage of a body cavity includes a second one-way valve mounted in said housing body between and in fluid communication with said inlet chamber and the inlet end of the sleeve of said first one-way elongated valve so as to prevent the passage of fluid between said inlet chamber and said first one-way elongated valve except through said second valve.

* * * * *